United States Patent [19]

Neuenschwander et al.

[11] Patent Number: 4,863,957
[45] Date of Patent: Sep. 5, 1989

[54] NOVEL HMG-COA REDUCTASE INHIBITORS

[75] Inventors: Kent W. Neuenschwander, Ambler, Pa.; John R. Regan, Princeton, N.J.; Benedict J. Kosmider, Audubon, Pa.

[73] Assignee: Rorer Pharmaceutical Corporation, Fort Washington, Pa.

[21] Appl. No.: 135,805

[22] Filed: Dec. 21, 1987

[51] Int. Cl.$^4$ .................. A61K 31/365; C07D 309/20
[52] U.S. Cl. .................................. 514/460; 549/292; 562/469
[58] Field of Search .................. 549/292, 570; 514/460

[56] References Cited

U.S. PATENT DOCUMENTS

| | | | |
|---|---|---|---|
| 4,282,155 | 8/1981 | Smith et al. | 549/292 |
| 4,308,378 | 12/1981 | Stataker | 549/292 |
| 4,503,072 | 3/1985 | Hoffman et al. | 549/292 |
| 4,622,338 | 11/1986 | Baran et al. | 514/460 |
| 4,772,626 | 9/1988 | Smith et al. | 549/292 |

Primary Examiner—Asok Pal

[57] ABSTRACT

Disclosed are novel 3-hydroxy-3-methylglutaryl-coenzyme A reductase inhibitors useful as antihypercholesterolemic agents represented by the formula

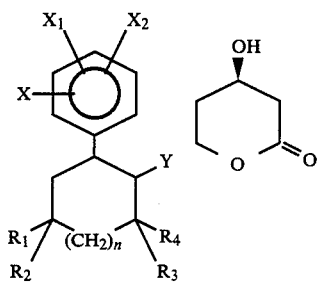

and the corresponding ring-opened hydroxy acids derived therefrom and pharmaceutically acceptable salts thereof.

Pharmaceutical compositions containing said compounds and method of inhibiting the biosynthesis of cholesterol therewith are also disclosed.

38 Claims, No Drawings

NOVEL HMG-COA REDUCTASE INHIBITORS

BACKGROUND OF THE INVENTION

1. Field of the Invention

The present invention relates to compounds, pharmaceutical compositions and a method useful for reducing serum cholesterol in humans. More particularly, the invention relates to trans-6-[(2-aryl-substituted cycloalkenyl and substituted cycloalkyl)alkenyl and alkyl]-3,4,5,6-tetrahydro-2H-pyran-2-ones, the corresponding ring opened hydroxy acids derived therefrom and pharmaceutically acceptable salts thereof which are potent inhibitors of the enzyme 3-hydroxy-3-methyl-glutaryl-coenzyme A reductase (hereinafter HMG CoA reductase), pharmaceutical compositions thereof, and a method of inhibiting biosynthesis of cholesterol for the treatment of atherosclerosis, hyperlipidemia and hypercholesterolemia.

2. Related Prior Art

Inhibitors of HMG-CoA are effective in lowering blood plasma cholesterol level as well as inhibiting the biosynthesis of cholesterol in humans. As such, inhibitors of HMG-CoA are useful in the prevention and treatment of coronary heart diseases. The prior art recognizes the importance of such compounds, e.g., Bethridge et al., Brit. Med. J., 4,500 (1975) and Brown et al., Scientific American, 58 Nov. (1984). Illustrative references directed to such compounds follow.

U.S. Pat. No. 4,681,893 to B. D. Roth pertains to trans-6-[2-(3-or 4-carboxamido-substituted pyrrol-1-yl)alkyl]- 4-hydroxypyran-2-ones useful as hypochloesterolemic agents.

U.S. Pat. No. 4,668,699 to Hoffman et al. discloses semi-synthetic analogs of compactin and mevinolin and the dihydro and tetrahydro analogs thereof for antihypercholesterolemic application.

U.S. Pat. No. 4,282,155 to Smith et al. is directed to 6(R)-[2-(8'-Etherified-hydroxy-2',6'-dimethylpolyhydronaphtyl-1')ethyl]-4(R)-hydroxy-3,4,5,6-tetrahydro-2H-pyran2-ones for inhibition of biosynthesis of cholesterol.

U.S. Pat. No. 4,567,289 relates to methyl, ethyl, n-propyl, 2-(acetylamino)ethyl, or 1-(2,3-dihydroxy)propyl ester of E-(3R,5S)-7-(4'-fluoro-3,3',5-trimethyl[1,1-'biphenyl]-2-yl)-3,5-dihydroxy-6-heptenoic acid that are HMG-CoA reductase inhibitors.

U.S. Pat. No. 4,611,067 discloses a process for the preparation of HMG-CoA reductase inhibitors which contain a 4-hydroxy-3,4,5,6-tetrahydro-2H-pyran-2-one moiety.

SUMMARY OF THE INVENTION

In accordance with the present invention, certain trans-6-[(2-aryl-substituted cycloalkenyl and substituted cycloalkyl)alkenyl and alkyl]-3,4,5,6-tetrahydro-2H-pyran-2-ones, the corresponding ring-opened hydroxy-acids derived therefrom and pharmaceutically acceptable salts thereof are provided which are potent inhibitors of HMG CoA reductase. Specifically, the invention provides compounds of formula I.

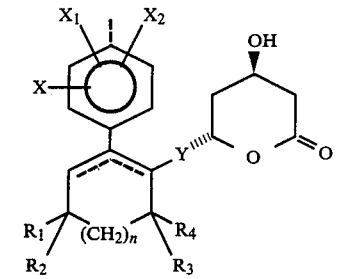

wherein
Y is:
—CHR—,
—CHRCHR—,
—CHRCHRCHR—, or
—RC=CR—;
X, $X_1$ and $X_2$ are independently:
H,
F,
Cl,
Br,
OH,
$CF_3$,
alkyl,
alkoxy,
aryl,
$NO_2$,
NH(CO)R,
$N(R)_2$, or
$S(O)_mR$;
$R_1$ and $R_2$ are independently:
H,
alkyl,
aryl,
OH,
OR,
F,
Cl, or
Br;
$R_3$ and $R_4$ are independently:
H or lower alkyl; R is
R is: H or lower alkyl;
n is: 0–2;
m is: 0–2; and
the dotted lines between carbons 1 and 2 or 2 and 3 in the cycloalkyl ring represent an optional double bond.

DETAILED DESCRIPTION OF THE INVENTION

As employed above and throughout the specification, the following terms, unless otherwise indicated, shall be understood to have the following meaning:

"Lower alkyl" means a saturated or unsaturated aliphatic hydrocarbon which may be either straight - or branched-chained containing from 1 to 4 carbon atoms.

"Alkyl" means a saturated or unsaturated aliphatic hydrocarbon which may be either straight-or branched-chained containing from about one to about six carbon atoms.

"Alkoxy" means an alkyl oxy group in which "alkyl" is as previously defined. Lower alkoxy groups are preferred which include methoxy, ethoxy, n-propoxy, i-propoxy, sec-propoxy, and n-butoxy.

"Aryl" means an aromatic hydrocarbon radical having 6 to 10 carbon atoms. The preferred aryl groups are phenyl, substituted phenyl and naphthyl. The term "substituted" means "alkyl" substitution.

The pharmaceutically acceptable salts of the present invention include those formed from sodium, potassium, calcium, aluminum, lithium, magnesium, zinc, lysine, arginine, procaine, ethylenediamine and piperazine.

The invention encompasses optical and stereoisomers of the compounds and mixtures thereof defined by the structural formula.

The general procedure for producing the compounds of the present invention is as follows:

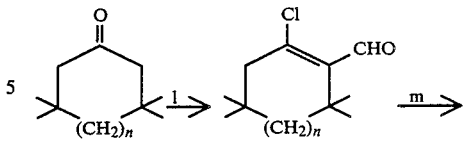

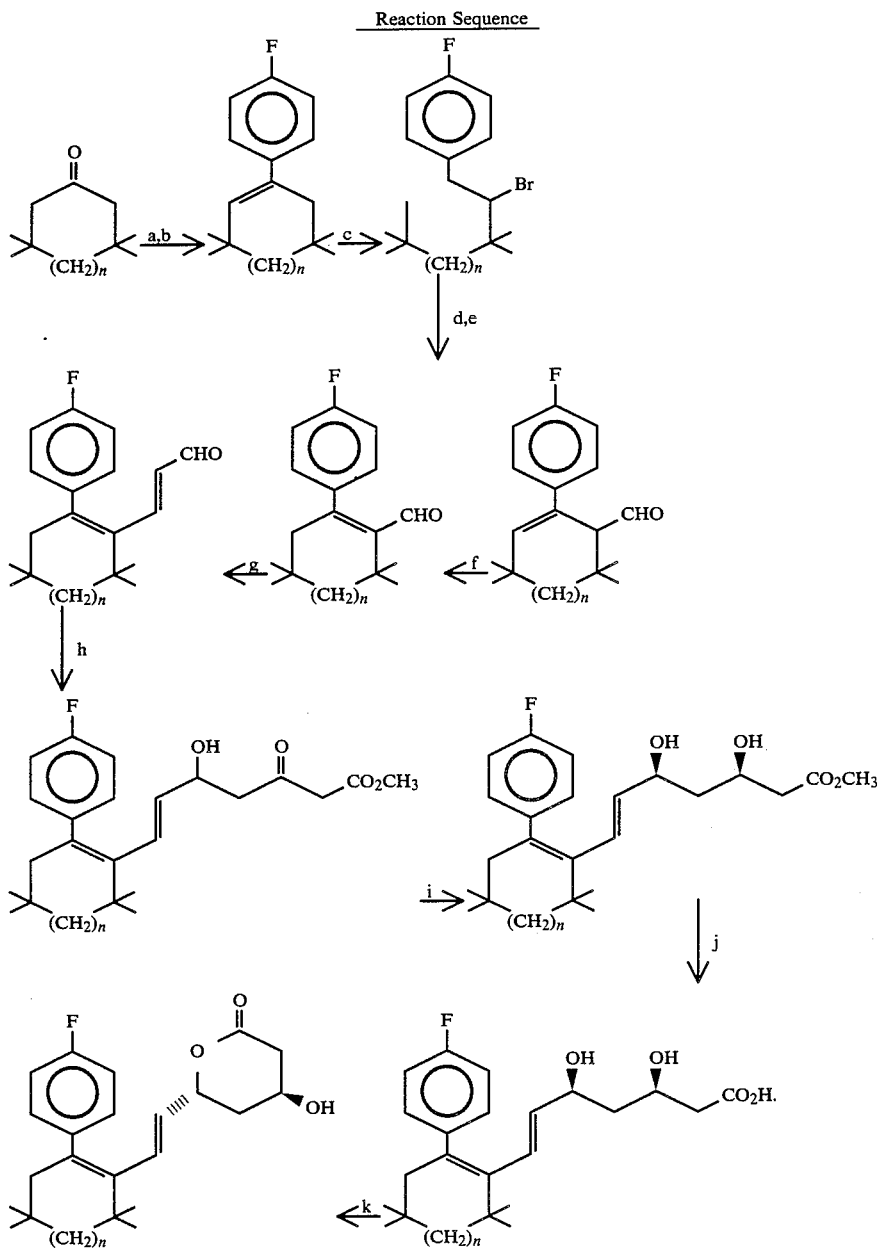

Alternatively, steps a through f can be replaced with steps and m as shown hereunder.

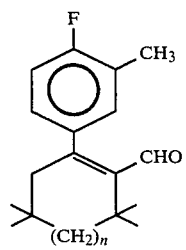

wherein the symbols used in the reactions denote the following reagents:

| | | | | | |
|---|---|---|---|---|---|
| a = | F—⟨○⟩—MgBr | b = | 50% H$_2$SO$_4$ | c = | N—bromosuccinimide |
| d = | Et$_2$N$^\ominus$CHCN | e = | (HO$_2$C)$_2$ | f = | Diazobicyclononane |
| g = | ⟨cyclohexyl⟩-N=CH$^\ominus$ | h = | $\overset{\ominus}{C}$H$_2$CO$\overset{\ominus}{C}$HCO$_2$CH$_3$ | i = | Et$_3$B, NaBH$_4$ |
| j = | NaOH, EtOH | k = | C$_6$H$_5$CH$_3$, heat | | |
| l = | Me$_2$NCHO, POCl$_3$ | m = | F—⟨○(CH$_3$)⟩—MgBr, Cu(OAC)$_2$ | | |

The starting materials were obtained from the Aldrich Chemical Co. but they may also be synthesized in accordance with methods known in the art.

The following preparative examples will further illustrate the invention.

EXAMPLE 1

Step 1: Preparation of 1-(4-fluorophenyl)-1-hydroxy-3,3,5,5-tetramethylcyclohexane A solution of 51.42g (333.3 mmoles) of 3,3,5,5-tetramethylcyclohexanone in 200 ml of tetrahydrofuran (THF) was added dropwise to an ice cold solution made up of 200 ml of a 2M ether solution of 4-fluorophenyl magnesium bromide (400 mmoles) and 100 ml of THF. The reaction mixture was warmed to room temperature and stirred overnight. The reaction mixture was then poured onto ice and 500 ml of 1N HCl. After stirring for 0.5 hour, the layers were separated. The aqueous layer was extracted once with ether and the combined organic layers were evaporated in vacuo to obtain the title compound in the form of an oil.

Step 2: Preparation of 1-(4-fluorophenyl)-3,3,5,5-tetramethylcyclohexene

From Step 1 the resulting oil was treated with 150 ml of ice cold 50% H$_2$SO$_4$. After stirring for 45 min. at room temperature, the reaction mixture was poured onto 900 ml of crushed ice and extracted with ether. The ether layer was extracted with saturated NaHCO$_3$ and brine. The ether was removed in vacuo and the resulting oil was distilled. BP 103°-106° C./1 mm Hg.

Step 3: Preparation of 1-Bromo-2-(4-fluorophenyl 4,4,6,6-tetramethylcyclohex-2-ene N-Bromosuccinimide (19.58 g, 110 mmoles) and benzoylperoxide (2.42 g, 10 mmoles) were added to a 0.5M CCl$_4$ solution of 23.2 g (100 mmoles) of the product from Step 2. The resulting mixture was heated at reflux for 0.5 hour. After cooling, the reaction mixture was filtered and the CCl$_4$ removed in vacuo. The resulting residue was chromatographed on silica gel, using hexane as the eluent. Yield 29.57 g (95.1 mmoles).

Step 4: Preparation of 2-Diethylamino-2-[2-(4-fluorophenyl)-4,4,6,6-tetramethylcyclohex-2-ene]acetonitrile To a stirred solution of diisopropyl amine (18.47 ml. 132 mmoles) in 250 ml of THF at −78° C. under nitrogen was added 48.4 ml (121 mmoles) of a 2.5M hexane solution of n-butyllithium.

After 15 minutes, a 2.0M THF solution of 14.25 ml (110 mmoles) of diethylaminoacetonitrile was added dropwise. After stirring for 15 minutes more, a 2.0M THF solution of the product obtained in Step 3 (100 mmoles) was added and the mixture slowly warmed to room temperature over a 3 hour period. The reaction mixture was poured into H$_2$O and extracted with ether. The organic layer was extracted with brine and the solvent evaporated in vacuo.

Step 5: Preparation of 2-(4-Fluorophenyl)-4,4,6,6-tetramethylcyclohex-2-ene-1-carboxaldehyde The residue from Step 4 was dissolved in 200 ml of THF and treated with a solution of 60 g of oxalic acid in 200 ml of H$_2$O. The resulting mixture was heated to reflux for 0.5 hour. After cooling the reaction mixture was poured into H$_2$O and extracted with ether. The ether layer was extracted twice with saturated NaHCO$_3$, evaporated in vacuo and the residue was purified by flash chromatography on silica gel. Overall yield 19.3 g (74.2 mmoles).

Step 6: Preparation of 2-(4-Fluorophenyl)-4,4,6,6-tetramethylcylohex-1-ene-1-carboxaldehyde The aldehyde obtained in Step 5 (130 g, 50 mmoles) was dissolved in a solution of 50 ml of THF and 50 ml of ethanol. To this solution was added 0.62 ml (5 mmles) of 1,5-diaza- bicylo-[4,3,0]-non-5-ene and the reaction mixture stirred at room temperature for 50 hours. The reaction mixture then was diluted with ether and extracted with dilute HCl, saturated NaHCO$_3$, and brine. The solvents were evaporated in vacuo and the residue purified by flash chromatography on silica gel.

Step 7: Preparation of (E)-3-[2-(4-Fluorophenyl)-4,4,6,6-tetramethylcyclohex-1-ene]-2-propenaldehyde To a stirred solution of diisopropylamine (10.07 ml, 72 mmoles), in 144 ml of THF, at −60° C., under nitrogen, was added 26.4 ml (66 mmoles) of a 2.5M hexane solution of n-butyllithium. After 15 minutes, when the temperature had warmed to −40° C., a 1.0M THF solution of ethylidenecyclohexylamine (7.5 g, 60 mmoles) was added dropwise. The reaction was stirred for 30 minutes, while the temperature rose to −10° C.

After stirring at −10° C. for an additional 10 minutes, the dark orange solution was cooled to -70° C. A 1.0M THF solution of the unsaturated aldehyde prepared in Step 6 (10.4 g, 40 mmoles) was added dropwise, allowed to slowly warm to −10° C and stirred for an additional hour.

The reaction mixture was poured into H₂O and extracted with ether. The organic layer was extracted with brine and the solvents evaporated in vacuo.

The crude intermediate was chromatographed on silica gel with hexane and finally hexane/ethyl acetate (20/1) as eluents. The intermediate 3-hydroxypropylidene cyclohexyl-amine was hydrolized on the silica gel column to the 2,4-dienal.

Step 8: Preparation of Methyl (E)-7-[2-(4-fluorophenyl)4,4,6,6-tetramethvlcyclohex-1-ene]-5-hydroxy-3-oxo-6heptenoate To a stirred solution of diisopropyl amine (12.09 ml, 86.4 mmoles), in 173 ml of THF, at −60° C., under nitrogen was added 31.68 ml (79.2 mmoles) of a 2.5M hexane solution of n-butyl₁ lithium. After 15 minutes, when the temperature had warmed to −40° C., methyl acetoacetate (3.89 ml, 36 mmoles) was added dropwise. The reaction mixture was stirred for 30 minutes while the temperature was allowed to warm to −10° C. to obtain a yellow solution of the dianion.

To the yellow solution of the dianion was added a 0.25M THF solution of 8.58 g (30 mmoles) of the aldehyde prepared in Step 7. The addition took 30 minutes. The reaction mixture was stirred an additional 30 minutes at −10° C, then quenched with 9.47 (165.6 mmoles) of acetic acid in 40 ml of THF. The reaction mixture was poured into ethyl acetate and extracted with H₂O, saturated NaHCO₃ and brine.

The residue was purified by flash chromatography on silica gel with hexane/ethyl acetate (5/1) as the eluent.

Step 9: Preparation of Methyl (E)-7-[2-(4-fluorophenyl)4,4,6,6-tetramethylcyclohex-1-ene]-3,5-dihydroxy-6-heptenoate The 5-hydroxy-3-keto ester (10.02 g, 24 mmoles) prepared in Step 8 was dissolved in 60 ml of dry THF and treated with triethylborane (1M in THF, 36 ml, 36 mmoles). After aging for 5 minutes at room temperature, the reaction mixture was cooled to −98° C. (MeOH-liquid N₂ bath). Sodium borohydride (1.04 g, 27.6 mmoles) was added, followed by dropwise addition of methanol (24 ml) over a 30 minute period. The reaction mixture was stirred for 30 minutes at −98° C. and over the next 30 minutes was allowed to warm to −60° C. At −60° C. the reaction mixture was quenched by the dropwise addition of 30% H₂O₂ (50 ml) in H₂O (125 ml).

The reaction mixture then was warmed to room temperature and stirred 30 minutes. It was poured into 1 liter ethyl acetate and extracted with 620 ml of 1N HCl. The organic layer was washed with saturated NaHCO₃ and brine.

Step 10: Preparation of (E)-7-[2-(4-Fluorophenyl)-4,4,6,6-tetramethylcyclohex-1-ene]-3,5-dihydroxy-6-heptenoic acid A 1N NaOH solution (30 ml, 30 mmoles) was added to a solution of the 3,5-dihydroxyester prepared in Step 9 (9.70 g, 24 mmoles) and 60 ml of ethanol. After stirring for 10 minutes, the ethanol was evaporated in vacuo. The residue was redissolved in H₂O and extracted twice with ether. The aqueous layer was acidified with 33 ml of 1N HCl and extracted twice with H₂CCl₂. The H₂CCl₂ was removed in vacuo.

Step 11: Preparation of trans-(E)-6-[2-[2-(4-Fluorophenyl)4,4,6,6-tetramethylcyclohex-1-ene]ethenyl]-3,4,5,6-tetrahydro-4-hydroxy-2H-pYran-2-one The 3,5-dihydroxycarboxylic acid from Step 10 (9.0 g, 23 mmoles) and 250 ml of toluene were refluxed in a Dean-Stark apparatus for 1.5 hour. The toluene was removed in vacuo and the residue chromatographed on silica gel using hexane/ethyl acetate (3/1) as the eluent. The product was recrystallized from ether/hexane. M.P. 121°–122° C.

Step 12: Preparation of (E)-7-[2-(4-Fluorophenyl)-4,4,6,6 tetramethylcyclohex-1-ene]-3,5-dihydroxy-6-heptenoic acid sodium salt To a solution of 1.17 g (3.14 mmoles) of the lactone prepared in Step 11, and 21 ml of ethanol was added 3.14 ml of 1N NaOH (3.14 mmoles). After stirring for 30 minutes, the ethanol was removed in vacuo. The residue was redissolved in 50 ml of HPLC grade H₂O and extracted twice with hexane. The water layer was freeze-dried to yield a white powder. M.P. 160°–190° C. (dec).

EXAMPLE 2

Referring to steps 1 and m of the reaction sequence, the following process can also be used to advantage subsequent to which the process described in steps 7 through 11 in Example 1 are to be followed.

Step 1: 2-Chloro-4,4,6,6-tetramethylcyclohex-1-ene-1-carboxaldehyde

Phosporus oxychloride (46.6 ml, 500 mmoles) was added dropwise over a 45 minute period, to an ice cold solution of 47.69 g (652 mmoles) of dimethylformamide and 45 ml of trichloroethylene. The reaction mixture was warmed to room temperature and stirred an additional 1.5 hours . To the resulting reaction mixture was added dropwise a solution of 77.13 g (500 mmoles) of 3,3,5,5-tetramethylcyclohexanone in 145 ml of trichloroethylene.

The reaction mixture was heated to 70° C. for 5 hours, then cooled and stirred overnight at room temperature.

The reaction mixture was cooled in an ice bath and treated dropwise with a solution of 185 g (2.25 moles) of sodium acetate in 400 ml of H₂O. The resulting layers were separated and the organic layer was washed once with 500 ml of H₂O and twice with 250 ml of brine. After drying over anhydrous sodium sulfate the mixture was filtered and the trichlorethylene removed in vacuo.

The concentrate was distilled through a vacuum-jacketed Vigreux column. BP 66°-70° C./1 mm Hg; Yield 26.4 (132 mmoles) of a light yellow oil.

Step 2:
2-(4-Fluoro-3-methylphenyl)-4,4,6,6-tetramethylcyclohex-1-ene-1-carboxaldehyde A Grignard reagent, freshly prepared from 55.96 g (296 mmoles) of 3-bromo-6-fluorotoluene, 11.39 ml (131.6 mmoles) of dibromethane, and 13.0 g (534.5 mmoles) of magnesium powder in 400 ml of dry THF was added slowly in an ice cold solution, under nitrogen, of 6.57 g (32.9 mmoles) of copper (II) acetate monohydrate, 26.4 g (131.6 mmoles) of 2-chloro-4,4,6,6-tetramethylcyclohex-1-ene-1-carboxaldehyde and 395 ml of dry THF.

During the addition of the Grignard reagent, the reaction mixture changed in color, from blue to a light yellow and finally a dark purple.

The addition took 2 hours and after stirring an additional 0.5 hour, at 0° C, the reaction was poured into 1 liter of saturated ammonium chloride. The organic layer was extracted with $H_2O$, brine, and dried over anhydrous magnesium sulfate. After filtering, the solution was concentrated in vacuo and the residue chomatographed on silica gel with hexane/ethyl acetate (40/1) as the eluent. Yield 17.85 g (65 mmoles).

Employing the general methods detailed in Examples 1 and 2 the following compounds can be prepared:
trans-6-[2-[2-(4-chlorophenyl)-4,4-dimethyl-6,6-diethyl-cyclohex-1-ene]ethyl]-3,4,5,6-tetrahydro-4-hydroxy-2H-pyran2-one;
trans-6-[2-[trans-2-(4-methylphenyl)-4,4,6,6-tetraethyl-cyclohexane]ethyl]-3,4,5,6-tetrahydro-4-hydroxy-2H-pyran2-one;
(E)-7-[2-(4-fluoro-3-methylphenyl)-4,4-diethyl-6,6dimethylcyclohex-2-ene]-3,5-dihydroxy-6-heptenoic acid;
7-[2-(3,4-dichlorophenyl)-4,4-dibutyl-6,6-dimethylcyclohex-1-ene]-3,5-dihydroxyheptanoic acid sodium salt;
ethyl-(E)-7-[cis-2-(3,5-dimethylphenyl)4,4-diphenyl-6,6-dimethylcyclohexane]-3,5-dihydroxy-6-heptenoate;
trans-(E)-6-[2-[2-(4-fluorophenyl)-4,4-dipropyl-6,6-dimethylcyclohex-1-ene]-ethenyl]-3,4,5,6-tetrahydro-4-hydroxy-2H-pyran-2-one;
trans-6-[2-[2-(4-chlorophenyl)-4,4-dimethyl-6,6-diethyl-cyclohex-1-ene]ethyl]-3,4,5,6-tetrahydro-4-hydroxy-2H-pyran-2-one;
trans-6-[2-[trans-2-(4-methylphenyl)-4,4,6,6-tetraethyl-cyclohexane]ethyl]-3,4,5,6-tetrahydro-4-hydroxy-2H-pyran2-one.
trans-(E)-6-[2-{2-(4-fluoro-3-methylphenyl)-4,4,6,6-tetramethylcyclohex-1-ene}ethenyl]-3,4,5,6-tetrahydro-4-hydroxy2H-pyran-2-one.

EXAMPLE 3

Using the starting materials 3,3,4,4-tetramethylcyclopentanone, 3-ethyl-4,4-dimethylcyclopentanone, 3-phenyl4,4-dimethylcyclopentanone, 3,4-diethylcyclopentanone and essentially following the process of either Example 1 or Example 2, the following five numbered ring compounds can be made, respectively:
trans-(E)-6-[2-{2-(4-fluorophenyl)-4,4,5,5-tetramethyl-cyclopent-1-ene}ethenyl]-3,4,5,6-tetrahydro-4-hydroxy-2H-pyran2-one;
trans-(E)-6-[2-{2-(4-fluorophenyl)-4-ethyl-5,5-dimethyl-cyclopent-1-ene}ethenyl]-3,4,5,6-tetrahydro-4-hydroxy-2H-pyran-2-one;
(E)-7-[2-(4-fluorophenyl)-4-phenyl-5,5-dimethylcyclopent1-ene]-3,5-dihydroxy-6-heptenoic acid sodium salt; and
(E)-7-[2-(4-fluorophenyl)-4,5-diethylcyclopent-1-ene]-3, 5-dihydroxy-6-heptenoic acid sodium salt.

EXAMPLE 4

Using the starting materials 3,3,6,6-tetramethylcycloheptanone, 3-phenyl-6,6-dimethylcycloheptanone, 3,6-dimethylcycloheptanone, 3,3-diethyl-6,6-dimethylcycloheptanone, and essentially following the process of either Example 1 or Example 2, the following seven membered ring compounds can be made, respectively:
trans-(E)-6-[2-{2-(4-fluorophenyl)-4,4,7,7-tetramethyl-cyclohept-1-ene}ethenyl]-3,4,5,6-tetrahydro-4-hydroxy-2H-pyran2-one;
trans-(E)-6-[2-{2-(4-fluorophenyl)-4-phenyl-7,7-dimethylcyclohept-1-ene}ethenyl]-3,4,5,6-tetrahydro-4-hydroxy-2H-pyran-2-one;
(E)-7-[2-(4-fluorophenyl)-4,7-dimethylcyclohept$_\pi$-1-ene]-3,5- dihydroxy-6-heptenoic acid sodium salt; and
(E)-7-[2-(4-fluorophenyl)-4,4-diethyl-7,7-dimethylcyclohept-1-ene]-3,5-dihydroxy-6-heptenoic acid sodium salt.

The compounds of the present invention are useful as hypocholesterolemic or hypolipidemic agents by virtue of their ability to inhibit the biosynthesis of cholesterol through inhibition of the enzyme HMG-CoA reductase. Having such ability, the compounds are incorporated into pharmaceutically acceptable carriers and administered to a patient in need of such cholesterol biosynthesis inhibition orally or parenterally. Such pharmaceutical formulations to contain at least one compound according to the invention.

Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, and glycerin and their combinations can be employed as well as other materials.

For parenteral administration, solutions or suspensions of these compounds in aqueous alcoholic media or in sesame or peanut oil or aqueous solutions of the soluble pharmaceutically acceptable salves can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of 5 mg/kg to 500 mg/kg of body weight in oral administration; such may, of course be given in two to four divided doses. With other forms of administration equivalent or adjusted doses will be administered depending on the route of administration.

The utility of the claimed compounds is measured by the test methods described hereunder. The methods are based on the articles: "Purification of 3-hydroxy-3-methylgutaryl-coenzyme A reductase from rat liver" by Kleinsek et al., Proc. Natl. Acad. Sci. USA, Vol. No. 4, pp. 1431–1435, April 1977 Biochemistry; "Mevinolin: A highly potent competitive inhibitor of hydroxy methyl glutaryl-coenzyme A reductase and a cholesterol-lowering agent" by Alberts et al., Proc. Natl. Acad. Sci. USA, Vol 77, pp. 3951–3961, July 1980, Biochemistry; "Effects of ML-236B on cholesterol metabolism in mice rats: Lack of hypocholesterolemic activity in normal animals" by Endo et al., Biochimica et Biophysica Acta, 575 (1979) 266–276; and "Evidence of regulation of 3-hydroxy-3-methylgluaryl coenzyme A reductase activity and cholesterol synthesis in monhepatic tissues of rat") by Balasubramaniam et al., Proc. Natl. Acad. Sci. USA, Vol. 73, No. 8, pp. 2564–2568, Aug. 1976, Biochemistry.

The first method used (designated HMGR Screen) was as follows. Male rats were acclimated to an alternate 12 hour light-dark cycle for a period of 2–3 weeks. The animals, weighing 180–230 g, were fed ad libitum a rat chow containing 2% cholestyramine for 5 days prior to sacrifice at the mid-dark period. Liver microsomes were prepared and HMGR enzyme was solubilized from the microsomes by freeze-thaw manipulation in high ionic strength buffer. The enzyme preparation was stored at −80° C. in 300 μl portion samples. Prior to use, the enzyme was activated at 37° C. for 30 minutes in a reaction mixture. The reaction mixture contained in a volume of 240 μl : 0.14M potassium phosphate buffer (pH 7.0); 0.18M KCl; 3.5 mM EDTA; 10 mM dithiothreitol; 0.1 mg/ml BSA; 30,000 cpm of [$^{14}$C] HMG CoA; 20 μM HMG CoA, and 200 μg of solubilized enzyme with and without inhibitors (in 10 μl DMSO). After 5 minutes incubation at 37° C the reaction was initiated with 0.2 mM NADPH. The final assay volume was 300 μl. The reaction then was terminated with 100 μl of 1N HCl. After an additional incubation for 15 minutes at 37° C. to allow for complete lactonization of the product, the mixture was diluted with 3 ml GDW. The diluted mixture was then poured over a 0.7×1.4 cm column containing 100–200 mesh Bio-Rex ion-exchange resin (cloride form of Bio-Rad) which was equilibrated with distilled water. With this resin the unreacted [$^{14}$C] HMG CoA was adsorbed and the product [$^{14}$C] lactone was eluted (80% recovery) directly into scintillation vials. After the addition of 10 ml of Aquasol ®, radioactivities of the samples were measured in a scintillation counter. Result on compound obtained in Example 1, Step 11 and compound obtained in Example 1, Step 12 is shown in Table I.

The second method (designated Ex-Vivo Non-Fasted and Ex-Vivo Fasted) used was as follows. Rats of 170–210 g were maintained on a low cholesterol diet for one week prior to use. Drugs (identified in Table I) were given orally in 0.5% methocel to both fed and fasted (fasted for 16 hours) rats. After one hour (fasted rats) and two hours (fed rats) the rats were decapitated and their livers removed and transferred to chilled oxygenated Kreb's-Ringer-bicarbonate buffer (pH 7.4). The livers were then chopped into 0.5 mm slices using a McIlwain tissue chopper, and were suspended in the same buffer. Aliquots of the suspension containing 100 mg tissue were pipetted to culture tubes which contained [$^{14}$C] sodium acetate (2 μCi, 1 mM). The tubes were gassed with 95% $O_2$/5% $CO_2$, capped and incubated at 37° C. in a shaking water bath at 150 oscillation/min. for two hours. The final assay volume was 1.0 ml. After incubation the reaction was stopped by the addition of 1.0 ml of 15% KOH in ethanol, and the internal standard $^3$H-cholesterol was added. The tubes were recapped and the samples were saponified at 75° C. for two hours with periodic mixing. Subsequently an aliquot was removed for protein analysis using Bio-Rad's standard kit, and the remainder of the saponified samples was extracted with 10 ml of petroleum ether for 30 minutes. The lower aqueous phase was frozen in a dry ice/alcohol mixture and the ether layer was poured into labelled tubes. The ether was then evaporated to dryness and the cholesterol was separated by thin layer chromatography on plastic silica gel plates. After visualization with iodine the cholesterol spots were cut and counted with liquid scintillation fluid. Result on compound of Example 1, Step 11 is shown in Table I.

TABLE I

| Assay | *$IC_{50}$ (Micromoles per liter) or **$ED_{50}$ (mg/kg) | |
|---|---|---|
| | Compound of Example 1 Step 11 | Compound of Example 1 Step 12 |
| HMGR Screen | 0.15 μM | 0.0034 μM |
| Ex Vivo Non-Fast | 11 mg/kg | |
| Ex Vivo Fasted | 1.2 mg/kg | |

*The micromolar concentration of compound required for 50% inhibition of cholesterol synthesis = $IC_{50}$
**The mg of drug per kg of body weight required for 50% inhibition of cholesterol synthesis = $ED_{50}$

What is claimed is:
1. A compound of the formula

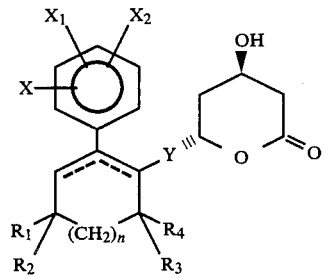

wherein
Y is
—CHR—,
—CHRCHR—,
—CHRCHRCHR—, or
—RC=CR—;
X,$X_1$ and $X_2$ are independently:

H,
F,
Cl,
Br,
OH,
$CF_3$,
alkyl,
alkoxy, or
aryl;

$R_1$ and $R_2$ are independently:
H,
alkyl,
aryl,
F,
Cl, or
Br;

$R_3$ and $R_4$ are independently: H or lower alkyl;
R is: H or lower alkyl;
n is: 0-2;
m is: 0-2;
its hydroxy acids; and
the pharmaceutically acceptable salts thereof.

2. A compound of claim 1 wherein X, $X_1$ and $X_2$ are alkyl of one to six carbon atoms.

3. A compound of claim 1 wherein X, $R_1$ and $R_2$ are alkyl of one to six carbon atoms.

4. A compound of claim 1 wherein $X_1$, $X_2$ and $X_3$ are alkoxy of one to six carbon atoms.

5. A compound of claim 1 wherein at least one of the X, $X_1$, $X_2$ $R_1$ and $R_2$ radicals is phenyl.

6. A compound of claim 1 wherein at least one of the X, $X_1$, $X_2$, $R_1$ and $R_2$ radicals is substituted phenyl.

7. A compound of claim 1 wherein at least one of the X, $X_1$, $X_2$ $R_1$ and $R_2$ radicals is naphthyl.

8. A compound of claim 1 wherein R is H.

9. A compound of claim 1 wherein R is lower alkyl having 1-4 carbon atoms.

10. A compound of claim 1 wherein R is methyl.

11. A compound of claim 1 wherein n is 1.

12. A compound of claim 1 wherein Y is —$CH_2$—.

13. A compound of claim 1 wherein Y is —$CH_2CH_2$—.

14. Trans-6-[2-[2-(4-fluorophenyl)-4,4,6,6-tetramethylcyclohex1-ene]ethyl]-3,4,5,6-tetrahydro-4-hydroxy-2H-pyran-2-one.

15. (E)-7-[2-(4-fluorophenyl)-4,4,6,6-tetramethylcyclohex-1-ene]3,5-dihydroxy-6-heptenoic acid sodium salt.

16. Trans-6-[2-[-2-(4-chlorophenyl)-4,4-dimethyl-6,6-diethylcyclohex-1-ene]ethyl]-3,4,5,6-tetrahydro-4-hydroxy-2H-pyran-2-one.

17. Trans-6-[2-[trans-2-(4-methylphenyl)-4,4,6,6-tetraethylcyclohexane]ethyl]-3,4,5,6-tetrahydro-4-hydroxy-2H-pyran2-one.

18. (E)-7-[2-(4-fluoro-3-methylphenyl)-4,4-diethyl-6,6-dimethylcyclohex-2-ene]-3,5-dihydroxy-6-heptenoic acid.

19. 7-[2-(3,4-dichlorophenyl)-4,4-dibutyl-6,6-dimethylcyclohex-1-ene]-3,5-dihydroxyheptanoic acid sodium salt.

20. Ethyl (E)-7-[cis-2-(3,5-dimethylphenyl)4,4-diphenyl-6,6-dimethylcyclohexane]-3,5-dihydroxy-6-heptenoate.

21. Trans-(E)-6-[2-[2-(4-fluorophenyl)-4,4,6,6-tetramethylcyclohex-1-ene]ethenyl]-3,4,5,6-tetrahydro-4-hydroxy-2H-pyran-2-one.

22. Trans-6-[2-[2-(4-chlorophenyl)-4,4 dimethyl-6,6-diethylcyclohex-1-ene]ethyl]-3,4,5,6-tetrahydro-4-hydroxy-2H-pyran-2-one.

23. Trans-6-[2-[trans-2-(4-methylphenyl)-4,4,6,6-tetraethylcyclohexane]ethyl]-3,4,5,6-tetrahydro-4-hydroxy-2H-pyran2-one.

24. Trans-E-6-[2-{2-(4-fluorophenyl)-4,4,5,5-tetramethylcyclopent-1-ene}ethenyl]-3,4,5,6-tetrahydro-4-hydroxy2H-pyran-2-one.

25. Trans-E-6-[2-{2-(4-fluorophenyl)-4-ethyl-5,5-dimethylcyclopent-1-ene}ethenyl]-3,4,5,6-tetrahydro-4-hydroxy-2H-pyran2-one.

26. (E)-7-[2-(4-fluorophenyl)-4-phenyl-5,5-dimethylcyclopent1-ene]-3,5-dihydroxy-6-heptenoic acid sodium salt.

27. (E)-7-[2-(4-fluorophenyl)-4,5-diethylcyclopent-1-ene]-3,5-dihydroxy-6-heptenoic acid sodium salt.

28. Trans-E-6-[2-{2-(4-fluorophenyl)-4-phenyl-7,7-dimethylcyclohept-1-ene}ethenyl]-3,4,5,6-tetrahydro-4-hydroxy-2H-pyran-2-one.

29. Trans-(E)-6-[2-{2-(4-fluorophenyl)-4-phenyl-7,7-dimethylcyclohept-1-ene}ethenyl]-3,4,5,6-tetrahydro-4-hydroxy-2H-pyran-one.

30. (E)-7-[2-(4-fluorophenyl)-4,7-dimethylcyclohept-1-ene]-3,5-dihydroxy-6-heptenoic acid sodium salt.

31. (E)-7-[2-(4-fluorophenyl)-4,4-diethyl-7,7-dimethylcyclohept1-ene]-3,5-dihydroxy-6-heptenoic acid sodium salt.

32. A hypocholesterolemic, hypolipidemic pharmaceutical composition comprising a therapeutically effective amount of a compound of claim 1 and a pharmaceutically acceptable carrier.

33. The hypocholesterolemic, hypolipidemic pharmaceutical composition of claim 32 wherein said compound is selected from the group consisting of:
trans-(E)-6-[2-[2-(4-fluorophenyl)-4,4,6,6-tetramethylcyclohex-1-ene]ethenyl]-3,4,5,6-tetrahydro-4-hydroxy-2H-pyran2-one;
(E)-7-[2-(4-fluorophenyl)-4,4,6,6-tetramethylcyclohex-1-ene]-3,5-dihydroxy-6-heptenoic acid sodium salt; and
trans-6-[2-[2-(4-chlorophenyl)-4,4-dimethyl-6,6-diethylcyclohex-1-ene]ethyl]-3,4,5,6-tetrahydro-4-hydroxy-2H-pyran-2-one.

34. The hypocholesterolemic, hypolipidemic pharmaceutical composition of claim 32 wherein said compound is selected from the group consisting of:
trans-6-[2-[trans-2-(4-methylphenyl)-4,4,6,6-tetraethylcyclohexane]ethyl]-3,4,5,6-tetrahydro-4-hydroxy-2H-pyran2-one;
(E)-7-[2-(4-fluoro-3-methylphenyl)-4,4-diethyl-6,6-diemethylcyclohex-2-ene]-3,5-dihydroxy-6-heptenoic acid; and
7-[2-(3,4-dichlorophenyl)-4,4-dibutyl-6,6-dimethylcyclohex-1-ene]-3,5-dihydroxyheptanoic acid sodium salt.

35. The hypocholesterolemic, hypolipidemic pharmaceutical composition of claim 32 wherein said compound is selected from the group consisting of:
ethyl (E)-7-[cis-2-(3,5-dimethylphenyl)-4,4-diphenyl-6,6-dimethylcyclohexane]-3,5-dihydroxy-6-heptenoate;
trans-(E)-6-[2-[2-(4-fluorophenyl)-4,4,6,6-tetramethylcyclohex-1-ene]ethenyl]-3,4,5,6-tetrahydro-4-hydroxy-2H-pyran-2-one;
trans-6-[2-[2-(4-chlorophenyl)-4,4 dimethyl-6,6-diethylcyclohex-1-ene]ethyl]-3,4,5,6-tetrahydro-4-hydroxy-2H-pyran-2-one; and trans-(E)-6-[2-{2-(4-fluoro-3-methylphenyl)-4,4,6,6-tetramethylcyclohex-1-ene}ethenyl]-3,4,5,6-tetrahydro-4-hydroxy2H-pyran-2-one.

36. The hypocholesterolemic, hypolipidemic pharmaceutical composition of claim 32 wherein said compound is selected from the group consisting of:

trans-E-6-[2-{2-(4-fluorophenyl)-4,4,5,5-tetramethylcyclopent-1-ene}ethenyl]-3,4,5,6-tetrahydro-4-hydroxy-2H-pyran2-one;

trans-E-6-[2-{2-(4-fluorophenyl)-4-ethyl-5,5-dimethylcyclopent-1-ene}ethenyl]-3,4,5,6-tetrahydro-4-hydroxy-2H-pyran2-one;

(E)-7-[2-(4-fluorophenyl)-4-phenyl-5,5-dimethylcyclopent1-ene]-3,5-dihydroxy-6-heptenoic acid sodium salt; and (E)-7-[2-(4-fluorophenyl)-4,5-diethylcyclopent-1-ene]-3, 5-dihydroxy-6-heptenoic acid sodium salt.

37. The hypocholesterolemic, hypolipidemic pharmaceutical composition of claim 32 hherein said compound is selected from the group consisting of:

trans-(E)-6-[2-(2-(4-fluorophenyl)-4,4,7,7-tetramethylcyclohept-1-ene}ethenyl]-3,4,5,6-tetrahydro-4-hydroxy-2H-pyran2-one;

trans-(E)-6-[2-{2-(4-fluorophenyl)-4-phenyl-7,7-dimethylcyclohept-1-ene}ethenyl]-3,4,5,6-tetrahydro-4-hydroxy-2H-pyran-2- one;

(E)-7-[2-(4-fluorophenyl)-4,7-dimethylcyclohept-1-ene]-3,5-dihydroxy-6-heptenoic acid sodium salt; and (E)-7-[2-(4-fluorophenyl)-4,4-diethyl-7,7-dimethylcyclohept1-ene]-3,5-dihydroxy-6-heptenoic acid sodium salt.

38. A method of inhibiting cholesterol biosynthesis in a patient in need of such treatment comprising administering a pharmaceutical composition defined in claim 32.

* * * * *